(12) United States Patent
Bryant

(10) Patent No.: US 8,292,150 B2
(45) Date of Patent: Oct. 23, 2012

(54) ADAPTER FOR POWERED SURGICAL DEVICES

(75) Inventor: Teddy R. Bryant, San Francisco, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/216,330

(22) Filed: Aug. 24, 2011

(65) Prior Publication Data

US 2012/0104071 A1   May 3, 2012

Related U.S. Application Data

(60) Provisional application No. 61/409,132, filed on Nov. 2, 2010.

(51) Int. Cl.
*A61B 17/068* (2006.01)
(52) U.S. Cl. ........ 227/175.1; 227/19; 606/167; 606/219
(58) Field of Classification Search ............... 227/19, 227/176.1, 180.1, 178.1, 175.1; 606/139, 606/219, 205, 208, 167
See application file for complete search history.

(56) References Cited

U.S. PATENT DOCUMENTS

| | | |
|---|---|---|
| 319,071 A | 6/1885 | Colesworthy |
| 529,401 A | 11/1894 | McCoy et al. |
| 931,327 A | 8/1909 | Manzel |
| 935,977 A | 10/1909 | Haskell |
| 948,492 A | 2/1910 | Avery |
| 986,829 A | 3/1911 | Kasperson |
| 1,372,577 A | 3/1921 | Wallenberg |
| 1,414,207 A | 4/1922 | Reed |
| 1,414,460 A | 5/1922 | Dixon |
| 1,629,547 A | 5/1927 | Smith |
| 1,666,292 A | 4/1928 | Knudsen |
| 1,708,378 A | 4/1929 | Dale |
| 1,859,426 A | 5/1932 | Beremand |
| 1,961,036 A | 5/1934 | Boyle |
| 2,251,470 A | 8/1941 | Stacey |
| 2,284,982 A | 6/1942 | Miller |
| 2,289,583 A | 7/1942 | Malone |
| 2,361,683 A | 10/1944 | Greenberg |
| 2,398,924 A | 4/1946 | Daniels |

(Continued)

FOREIGN PATENT DOCUMENTS

EP        0 634 144 A1    1/1995

(Continued)

OTHER PUBLICATIONS

European Search Report for corresponding EP11250771 date of mailing is Feb. 17, 2012 (3 pgs).

(Continued)

*Primary Examiner* — Scott A. Smith

(57) ABSTRACT

An adapter assembly for selectively interconnecting a surgical end effector including at least one axially translatable drive member and a powered actuator device including at least one rotatable drive shaft is provided. The adapter assembly includes an actuation shaft configured to convert rotation of a first drive shaft of the powered actuator device into an axial translation of a first drive member of the surgical end effector. The adapter assembly further includes an elongate tube configured to convert rotation of a second drive shaft of the powered actuator device into an axial translation of a second drive member of the surgical end effector. The actuation shaft is disposed within the elongate tube, and the actuation shaft and the elongate tube translate axially independent of each other.

14 Claims, 5 Drawing Sheets

U.S. PATENT DOCUMENTS

| | | |
|---|---|---|
| 2,399,536 A | 4/1946 | Baum |
| 2,407,471 A | 9/1946 | Burk |
| 2,421,174 A | 5/1947 | Wyrick |
| 2,432,860 A | 12/1947 | Clatfelter |
| 2,449,284 A | 9/1948 | Dorman |
| 2,465,309 A | 3/1949 | Happe et al. |
| 2,478,195 A | 8/1949 | Hull |
| 2,482,995 A | 9/1949 | Willis |
| 2,483,662 A | 10/1949 | Niederhiser |
| 2,485,799 A | 10/1949 | Woytych |
| 2,511,416 A | 6/1950 | Rundorff |
| 2,529,396 A | 11/1950 | Hunt |
| 2,588,267 A | 3/1952 | McLaughlin |
| 2,598,477 A | 5/1952 | Wilberschied |
| 2,616,274 A | 11/1952 | Landrum |
| 2,676,025 A | 4/1954 | Davis |
| 2,680,634 A | 6/1954 | Haworth et al. |
| 2,695,787 A | 11/1954 | Sunnen |
| 2,709,600 A | 5/1955 | Lehde |
| 2,714,026 A | 7/1955 | Schultz |
| 2,719,722 A | 10/1955 | Nickless |
| 2,729,076 A | 1/1956 | Thomson |
| 2,730,220 A | 1/1956 | Dodd |
| 2,730,876 A | 1/1956 | Russell |
| 2,731,006 A | 1/1956 | Hensel |
| 2,777,340 A | 1/1957 | Hettwer et al. |
| 2,783,050 A | 2/1957 | Garrison et al. |
| 2,805,073 A | 9/1957 | Fletcher |
| 2,850,287 A | 9/1958 | Jackson |
| 2,851,295 A | 9/1958 | Chaffee |
| 2,857,166 A | 10/1958 | Conn et al. |
| 2,893,221 A | 7/1959 | Bell |
| 2,893,274 A | 7/1959 | Mueller et al. |
| 2,918,290 A | 12/1959 | Werstein |
| 2,918,291 A | 12/1959 | Plantas |
| 2,931,659 A | 4/1960 | Novkov |
| 2,940,765 A | 6/1960 | Appleby |
| 2,957,353 A | 10/1960 | Babacz |
| 2,998,258 A | 8/1961 | Ambrose |
| 3,023,015 A | 2/1962 | Pankow |
| 3,026,116 A | 3/1962 | Marini, Sr. |
| 3,064,502 A | 11/1962 | Pittwood |
| 3,111,328 A | 11/1963 | Di Rito et al. |
| 3,111,329 A | 11/1963 | Steinmann |
| 3,129,950 A | 4/1964 | Galler |
| 3,136,563 A | 6/1964 | Swanson et al. |
| 3,150,725 A | 9/1964 | Hornschuch et al. |
| 3,159,081 A | 12/1964 | Erikson |
| 3,202,433 A | 8/1965 | Davis |
| 3,210,962 A | 10/1965 | Birdwell |
| 3,211,485 A | 10/1965 | Petersen |
| 3,360,861 A | 1/1968 | Hoffman |
| 3,368,369 A | 2/1968 | Kimmel |
| 3,368,371 A | 2/1968 | Herman, Jr. |
| 3,383,883 A | 5/1968 | Dutaret |
| 3,506,277 A | 4/1970 | Harms |
| 3,516,311 A | 6/1970 | Marca |
| 3,521,507 A | 7/1970 | Yogus et al. |
| 3,540,748 A | 11/1970 | Buck |
| 3,553,980 A | 1/1971 | Dickinson et al. |
| 3,571,886 A | 3/1971 | Corsmeier |
| 3,610,643 A | 10/1971 | Thompson |
| 3,612,552 A | 10/1971 | Brundler |
| 3,657,941 A | 4/1972 | Engler |
| 3,658,352 A | 4/1972 | Koch et al. |
| 3,663,028 A | 5/1972 | King, Jr. et al. |
| 3,664,677 A | 5/1972 | Sunderman et al. |
| 3,680,435 A | 8/1972 | Deplante |
| 3,695,058 A | 10/1972 | Keith, Jr. |
| 3,696,984 A | 10/1972 | Fitchen |
| 3,707,301 A | 12/1972 | Rauls |
| 3,716,246 A | 2/1973 | Peterson |
| 3,724,237 A | 4/1973 | Wood |
| 3,730,540 A | 5/1973 | King, Jr. et al. |
| 3,734,515 A | 5/1973 | Dudek |
| 3,741,573 A | 6/1973 | Treer |
| 3,742,656 A | 7/1973 | Amos |
| 3,744,807 A | 7/1973 | Spires et al. |
| 3,746,353 A | 7/1973 | Allen |
| 3,747,946 A | 7/1973 | Edens |
| 3,750,498 A | 8/1973 | Willen |
| 3,750,671 A | 8/1973 | Hedrick |
| 3,752,595 A | 8/1973 | Woythal et al. |
| 3,756,737 A | 9/1973 | Smith |
| 3,758,125 A | 9/1973 | Cornelia |
| 3,759,336 A | 9/1973 | Marcovitz et al. |
| 3,779,063 A | 12/1973 | Gannon |
| 3,788,656 A | 1/1974 | Smith |
| 3,788,658 A | 1/1974 | Benjamin et al. |
| 3,815,380 A | 6/1974 | Esmay |
| 3,815,928 A | 6/1974 | Komori |
| 3,828,580 A | 8/1974 | Armbruster |
| 3,837,759 A | 9/1974 | Bittern |
| 3,843,143 A | 10/1974 | Laxson |
| 3,854,536 A | 12/1974 | Hallock, Jr. |
| 3,874,688 A | 4/1975 | Schiller |
| 3,884,120 A | 5/1975 | Diferdinando |
| 3,907,312 A | 9/1975 | Fletcher et al. |
| 3,913,952 A | 10/1975 | Matsui et al. |
| 3,945,221 A | 3/1976 | Miokovic |
| 3,955,377 A | 5/1976 | Bendall |
| 3,973,784 A | 8/1976 | Smith |
| 3,977,687 A | 8/1976 | Manganelli |
| 3,985,368 A | 10/1976 | Better et al. |
| 3,998,372 A | 12/1976 | Leonardo et al. |
| 4,006,996 A | 2/1977 | Kasabian |
| 4,007,795 A | 2/1977 | Gawron et al. |
| 4,017,934 A | 4/1977 | Callahan |
| 4,018,062 A | 4/1977 | Bulliot |
| 4,019,344 A | 4/1977 | Calistrat |
| 4,023,405 A | 5/1977 | Larson |
| 4,035,100 A | 7/1977 | Kruger et al. |
| D245,395 S | 8/1977 | Cognevich |
| 4,069,826 A | 1/1978 | Sessions et al. |
| 4,109,488 A | 8/1978 | Work |
| 4,158,522 A | 6/1979 | Wirfelt |
| 4,171,821 A | 10/1979 | Miller |
| 4,176,991 A | 12/1979 | Egli |
| 4,192,320 A | 3/1980 | Megahed |
| 4,197,886 A | 4/1980 | MacDonald |
| 4,224,969 A | 9/1980 | Plessner |
| 4,237,659 A | 12/1980 | Welsch et al. |
| 4,237,703 A | 12/1980 | Wahl, Jr. |
| 4,238,167 A | 12/1980 | Brugger et al. |
| 4,254,674 A | 3/1981 | Strussion et al. |
| 4,274,269 A | 6/1981 | Trabue |
| 4,274,774 A | 6/1981 | Haga et al. |
| D260,355 S | 8/1981 | Buzzell |
| 4,292,027 A | 9/1981 | Richmond |
| 4,298,208 A | 11/1981 | Benjamin |
| 4,349,023 A | 9/1982 | Gross |
| 4,349,929 A | 9/1982 | Dewey |
| 4,362,166 A | 12/1982 | Furler et al. |
| 4,365,397 A | 12/1982 | Felpel |
| 4,384,669 A | 5/1983 | Welsh |
| 4,392,499 A | 7/1983 | Towse |
| 4,398,886 A | 8/1983 | Schuss et al. |
| 4,412,096 A | 10/1983 | Edgerton et al. |
| 4,434,927 A | 3/1984 | Butler et al. |
| 4,436,463 A | 3/1984 | Rea |
| 4,447,177 A | 5/1984 | Ochiai et al. |
| 4,449,953 A | 5/1984 | Nikomarov et al. |
| 4,452,592 A | 6/1984 | Tsai |
| 4,477,095 A | 10/1984 | Atkinson, III |
| 4,492,230 A | 1/1985 | Sunago et al. |
| 4,496,163 A | 1/1985 | Bernfeld |
| 4,500,235 A | 2/1985 | Johnsen |
| 4,504,227 A | 3/1985 | Löhn |
| 4,559,043 A | 12/1985 | Whitehouse et al. |
| 4,560,310 A | 12/1985 | Eckstein et al. |
| 4,570,633 A | 2/1986 | Golden |
| 4,575,015 A | 3/1986 | Sugioka et al. |
| 4,575,359 A | 3/1986 | Bermingham |
| 4,597,699 A | 7/1986 | Ramunas |
| 4,614,137 A | 9/1986 | Jones |
| 4,616,651 A | 10/1986 | Golden |
| 4,645,453 A | 2/1987 | Niznick |

| | | | | | |
|---|---|---|---|---|---|
| 4,647,051 A | 3/1987 | Stone et al. | 5,476,379 A | 12/1995 | Disel |
| 4,655,631 A | 4/1987 | Mitchell | 5,489,205 A | 2/1996 | Davis et al. |
| 4,661,009 A | 4/1987 | Tripp | 5,501,542 A | 3/1996 | Hall, Sr. |
| 4,668,138 A | 5/1987 | Carter | 5,507,787 A | 4/1996 | Borghi |
| 4,674,172 A | 6/1987 | Botimer | 5,509,489 A | 4/1996 | Lower, Jr. |
| 4,685,687 A | 8/1987 | Hall et al. | 5,514,113 A | 5/1996 | Anderson et al. |
| 4,688,810 A | 8/1987 | Waite | 5,549,657 A | 8/1996 | Stern et al. |
| 4,691,429 A | 9/1987 | Goodsmith | 5,564,717 A | 10/1996 | Alberts |
| 4,708,548 A | 11/1987 | Taylor et al. | 5,570,445 A | 10/1996 | Chou et al. |
| 4,710,079 A | 12/1987 | Smith et al. | 5,586,847 A | 12/1996 | Mattern, Jr. et al. |
| 4,722,645 A | 2/1988 | Regan | 5,615,590 A | 4/1997 | Speckhahn |
| 4,750,750 A | 6/1988 | Batalorf, Jr. | 5,653,694 A | 8/1997 | Powles et al. |
| 4,772,245 A | 9/1988 | Readman et al. | 5,658,192 A | 8/1997 | Reinauer |
| 4,777,714 A | 10/1988 | Blessing | 5,667,228 A | 9/1997 | Fabris |
| 4,781,654 A | 11/1988 | Walter et al. | 5,676,028 A | 10/1997 | Jordan |
| 4,786,221 A | 11/1988 | March | 5,678,961 A | 10/1997 | Fleege et al. |
| 4,793,053 A | 12/1988 | Zuccaro et al. | 5,693,025 A | 12/1997 | Stevens |
| 4,795,291 A | 1/1989 | March | 5,701,910 A | 12/1997 | Powles et al. |
| 4,809,995 A | 3/1989 | Ramunas | 5,704,838 A | 1/1998 | Teale |
| 4,810,139 A | 3/1989 | Regan | 5,709,605 A | 1/1998 | Riefe et al. |
| 4,815,347 A | 3/1989 | Rogers | 5,711,709 A | 1/1998 | McCoy |
| 4,818,157 A | 4/1989 | Kouvelis | 5,716,056 A | 2/1998 | Bokram |
| 4,824,298 A | 4/1989 | Lippacher et al. | 5,730,657 A | 3/1998 | Olgren |
| 4,834,596 A | 5/1989 | Hollifield et al. | 5,741,134 A | 4/1998 | Davis |
| 4,836,826 A | 6/1989 | Carter | 5,743,431 A | 4/1998 | Brattesani |
| 4,838,361 A | 6/1989 | O'Toole | 5,746,724 A | 5/1998 | Powles et al. |
| 4,840,520 A | 6/1989 | Pfalzgraf | 5,775,857 A | 7/1998 | Johne |
| 4,861,203 A | 8/1989 | Bassett et al. | 5,785,229 A | 7/1998 | Franzini |
| 4,861,313 A | 8/1989 | Zeiser et al. | 5,800,391 A | 9/1998 | Kontos |
| 4,870,743 A | 10/1989 | Gilmore | 5,806,859 A | 9/1998 | Saccomanno, III |
| 4,874,181 A | 10/1989 | Hsu | 5,836,727 A | 11/1998 | Scheer |
| 4,879,930 A | 11/1989 | von Haas | 5,863,159 A | 1/1999 | Lasko |
| 4,886,402 A | 12/1989 | Pfalzgraf | 5,876,381 A | 3/1999 | Pond et al. |
| 4,910,860 A | 3/1990 | Winkler et al. | 5,893,689 A | 4/1999 | Juhasz |
| 4,913,607 A | 4/1990 | von Haas | 5,901,967 A | 5/1999 | Morisaki |
| 4,919,023 A | 4/1990 | Bloink | 5,902,280 A | 5/1999 | Powles et al. |
| 4,938,731 A | 7/1990 | Nguyen et al. | 5,913,845 A | 6/1999 | Brimhall |
| 4,941,861 A | 7/1990 | Painter | 5,921,563 A | 7/1999 | Huggins et al. |
| 4,946,177 A | 8/1990 | Barbieux | 5,928,241 A | 7/1999 | Menut et al. |
| 4,958,966 A | 9/1990 | Andrews | 5,931,737 A | 8/1999 | Aota et al. |
| 4,958,968 A | 9/1990 | von Haas et al. | 5,944,331 A | 8/1999 | Kim |
| 4,969,863 A | 11/1990 | van't Hooft et al. | 5,957,634 A | 9/1999 | Carpinetti |
| 4,995,768 A | 2/1991 | Craft | 5,957,636 A | 9/1999 | Boisvert |
| 4,998,934 A | 3/1991 | Bernstein | 5,984,595 A | 11/1999 | Mizoguchi |
| 5,011,344 A | 4/1991 | Johnson | 5,984,596 A | 11/1999 | Fehrle et al. |
| 5,015,129 A | 5/1991 | Albin | 5,993,454 A | 11/1999 | Longo |
| 5,033,921 A | 7/1991 | Yasuhara et al. | 6,003,416 A | 12/1999 | Ando et al. |
| 5,049,071 A | 9/1991 | Davis et al. | 6,033,162 A | 3/2000 | Uebele et al. |
| 5,052,496 A | 10/1991 | Albert et al. | 6,035,512 A | 3/2000 | Cook |
| 5,062,749 A | 11/1991 | Sheets | 6,042,310 A | 3/2000 | Campbell et al. |
| 5,098,416 A | 3/1992 | Imonti | 6,062,574 A | 5/2000 | Yorde |
| 5,110,145 A | 5/1992 | Stewart | 6,062,779 A | 5/2000 | Sugimura |
| 5,129,118 A | 7/1992 | Walmesley | 6,074,304 A | 6/2000 | Olbrich et al. |
| 5,135,060 A | 8/1992 | Ide | 6,086,292 A | 7/2000 | Yokoyama |
| 5,137,495 A | 8/1992 | Luebke | 6,098,726 A | 8/2000 | Taylor et al. |
| 5,173,017 A | 12/1992 | Oshnock et al. | 6,109,620 A | 8/2000 | Roberts et al. |
| 5,180,261 A | 1/1993 | Schreiber | 6,126,549 A | 10/2000 | Appell et al. |
| 5,190,422 A | 3/1993 | Léchot | 6,129,547 A | 10/2000 | Cise et al. |
| 5,190,529 A | 3/1993 | McCrory et al. | 6,142,878 A | 11/2000 | Barin |
| 5,191,666 A | 3/1993 | Corbin | 6,145,851 A | 11/2000 | Heber |
| 5,192,206 A | 3/1993 | Davis et al. | 6,152,826 A | 11/2000 | Profeta et al. |
| 5,193,826 A | 3/1993 | Smith | 6,155,576 A | 12/2000 | Yorde |
| 5,203,595 A | 4/1993 | Borzone et al. | 6,159,102 A | 12/2000 | Hennessey et al. |
| 5,209,219 A | 5/1993 | Hollobaugh | 6,161,937 A | 12/2000 | Rosenstatter |
| 5,219,174 A | 6/1993 | Zurbriigg et al. | 6,171,033 B1 | 1/2001 | Wrobel |
| 5,224,898 A | 7/1993 | Johnson et al. | 6,179,300 B1 | 1/2001 | Baumann et al. |
| 5,236,356 A | 8/1993 | Davis et al. | 6,179,303 B1 | 1/2001 | Jansen |
| 5,238,341 A | 8/1993 | Horsch | 6,186,712 B1 | 2/2001 | Senzaki |
| 5,282,638 A | 2/1994 | Harper | 6,190,395 B1 | 2/2001 | Williams |
| 5,306,146 A | 4/1994 | Davis et al. | 6,193,241 B1 | 2/2001 | Robison |
| 5,318,529 A | 6/1994 | Kontos | 6,193,242 B1 | 2/2001 | Robison |
| 5,330,206 A | 7/1994 | Krumszyn et al. | 6,200,220 B1 | 3/2001 | Drew |
| 5,342,195 A | 8/1994 | Davis et al. | 6,203,435 B1 | 3/2001 | Falgout, Sr. |
| 5,352,074 A | 10/1994 | Ishikawa | 6,213,071 B1 | 4/2001 | Lancefield et al. |
| 5,368,421 A | 11/1994 | Head | 6,217,453 B1 | 4/2001 | Thompson |
| 5,392,662 A | 2/1995 | Jadrich et al. | 6,224,304 B1 | 5/2001 | Smith et al. |
| 5,431,661 A | 7/1995 | Koch | 6,231,450 B1 | 5/2001 | Korus |
| 5,439,005 A | 8/1995 | Vaughn | 6,241,434 B1 | 6/2001 | Ajimi |
| 5,447,472 A | 9/1995 | Ide | 6,250,856 B1 | 6/2001 | Miyanaga |

| | | |
|---|---|---|
| 6,253,720 B1 | 7/2001 | Lancefield et al. |
| 6,260,281 B1 | 7/2001 | Okumura et al. |
| 6,264,408 B1 | 7/2001 | Lung et al. |
| 6,276,065 B1 | 8/2001 | Osada et al. |
| 6,287,059 B1 | 9/2001 | Hashidate et al. |
| 6,287,117 B1 | 9/2001 | Niznick |
| 6,287,203 B1 | 9/2001 | Chen et al. |
| 6,287,207 B1 | 9/2001 | Rui et al. |
| 6,293,559 B1 | 9/2001 | Harman, Jr. et al. |
| 6,296,096 B1 | 10/2001 | Chludek |
| 6,299,538 B1 | 10/2001 | Gassmann |
| 6,302,311 B1 * | 10/2001 | Adams et al. ............... 227/176.1 |
| 6,302,409 B1 | 10/2001 | Gutsche |
| 6,305,519 B1 | 10/2001 | Katoh et al. |
| 6,308,669 B1 | 10/2001 | Lancefield et al. |
| 6,312,255 B1 | 11/2001 | Hudak |
| 6,312,339 B1 | 11/2001 | Beyert |
| 6,315,060 B1 | 11/2001 | Schuda et al. |
| 6,321,855 B1 | 11/2001 | Barnes |
| 6,343,731 B1 * | 2/2002 | Adams et al. ............... 227/180.1 |
| 6,357,974 B1 | 3/2002 | Robins |
| 6,368,324 B1 | 4/2002 | Dinger et al. |
| 6,371,705 B1 | 4/2002 | Gaudreau |
| 6,375,577 B1 | 4/2002 | Smith et al. |
| 6,378,630 B1 | 4/2002 | Ritorto et al. |
| 6,464,589 B1 | 10/2002 | Shinozuka |
| 6,478,681 B1 | 11/2002 | Overaker et al. |
| 6,484,859 B2 | 11/2002 | Chludek |
| 6,506,120 B1 | 1/2003 | Lockwood |
| 6,510,970 B2 | 1/2003 | McLean et al. |
| 6,511,268 B1 | 1/2003 | Vasudeva et al. |
| 6,511,321 B1 | 1/2003 | Trushkowsky et al. |
| 6,517,560 B1 | 2/2003 | Toth et al. |
| 6,533,157 B1 * | 3/2003 | Whitman .................... 227/175.1 |
| 6,533,578 B2 | 3/2003 | Segal |
| 6,537,280 B2 | 3/2003 | Dinger et al. |
| 6,554,288 B2 | 4/2003 | Tomoni |
| 6,554,290 B2 | 4/2003 | Lin |
| 6,569,118 B2 | 5/2003 | Johnson et al. |
| 6,569,163 B2 | 5/2003 | Hata et al. |
| 6,585,462 B1 | 7/2003 | Göransson |
| 6,604,744 B2 | 8/2003 | Monge |
| 6,610,066 B2 | 8/2003 | Dinger et al. |
| 6,612,586 B2 | 9/2003 | Liou |
| 6,615,835 B1 | 9/2003 | Cise et al. |
| 6,616,446 B1 | 9/2003 | Schmid |
| 6,619,413 B2 | 9/2003 | Hamilton et al. |
| 6,640,150 B1 | 10/2003 | Persson et al. |
| 6,640,679 B1 | 11/2003 | Roberts, Jr. |
| 6,640,911 B2 | 11/2003 | Lieser et al. |
| 6,663,493 B1 | 12/2003 | Chen |
| 6,666,114 B1 | 12/2003 | Lin |
| 6,669,568 B1 | 12/2003 | Neuner et al. |
| 6,679,365 B2 | 1/2004 | Katoh et al. |
| 6,702,680 B2 | 3/2004 | Sullivan et al. |
| 6,716,028 B2 | 4/2004 | Rahman et al. |
| 6,722,038 B2 | 4/2004 | Visman et al. |
| 6,725,004 B2 | 4/2004 | Ahn et al. |
| 6,755,424 B1 | 6/2004 | Paulsen |
| 6,761,361 B2 | 7/2004 | Taylor et al. |
| 6,769,846 B2 | 8/2004 | Campbell, Jr. et al. |
| 6,808,345 B2 | 10/2004 | Kato |
| 6,817,508 B1 | 11/2004 | Racenet et al. |
| 6,824,566 B2 | 11/2004 | Kana et al. |
| 6,825,630 B2 | 11/2004 | Katoh et al. |
| 6,854,740 B2 | 2/2005 | Baumann et al. |
| 6,854,741 B2 | 2/2005 | Lopez |
| 6,893,026 B2 | 5/2005 | Yoshimura et al. |
| 6,899,538 B2 | 5/2005 | Matoba |
| 6,915,865 B2 | 7/2005 | Boyd |
| 6,916,248 B1 | 7/2005 | Burgess |
| 6,926,526 B2 | 8/2005 | Hudak |
| 6,935,636 B2 | 8/2005 | Bobst |
| 6,935,637 B2 | 8/2005 | Cantlon |
| 6,955,660 B2 | 10/2005 | Fisher |
| 7,011,661 B2 | 3/2006 | Riedel et al. |
| 7,014,464 B2 | 3/2006 | Niznick |
| 7,018,298 B1 | 3/2006 | Chiou |
| 7,032,798 B2 * | 4/2006 | Whitman et al. .......... 227/175.1 |
| 7,121,951 B2 | 10/2006 | Chang |
| 7,137,185 B2 | 11/2006 | Voss et al. |
| 7,144,326 B2 | 12/2006 | Thompson |
| 7,150,680 B2 | 12/2006 | White |
| 7,153,214 B2 | 12/2006 | Delaney et al. |
| 7,182,558 B2 | 2/2007 | Haimer |
| 7,192,355 B2 | 3/2007 | Bayer et al. |
| 7,195,247 B2 | 3/2007 | Shu |
| 7,204,804 B2 | 4/2007 | Zirps et al. |
| 7,217,072 B1 | 5/2007 | Haimer |
| 7,228,767 B2 | 6/2007 | Chang |
| 7,243,572 B1 | 7/2007 | Arling et al. |
| 7,267,548 B2 | 9/2007 | Ponzini |
| 7,270,568 B2 | 9/2007 | Osypka |
| 7,272,345 B2 | 9/2007 | Kim et al. |
| 7,284,936 B1 | 10/2007 | Rinner |
| 7,300,042 B2 | 11/2007 | McClure |
| 7,316,529 B2 | 1/2008 | Phillips et al. |
| 7,331,585 B2 | 2/2008 | Lindstrom |
| 7,331,738 B2 | 2/2008 | Hofbrucker et al. |
| 7,334,970 B2 | 2/2008 | Kozak |
| 7,338,420 B2 | 3/2008 | Imahata |
| 7,347,828 B2 | 3/2008 | Francese et al. |
| 7,354,230 B2 | 4/2008 | Bauman |
| 7,371,034 B2 | 5/2008 | Clark |
| 7,374,377 B2 | 5/2008 | Bauman |
| 7,431,587 B2 | 10/2008 | Pond |
| 7,464,849 B2 * | 12/2008 | Shelton et al. ............. 227/178.1 |
| 7,488,134 B2 | 2/2009 | Kinme et al. |
| 7,491,058 B2 | 2/2009 | Jorneus et al. |
| 7,494,304 B2 | 2/2009 | McAuliffe |
| 7,506,877 B1 | 3/2009 | Henderson et al. |
| 7,534,104 B2 | 5/2009 | Schneider |
| 7,549,564 B2 * | 6/2009 | Boudreaux ................ 227/179.1 |
| 7,549,953 B2 | 6/2009 | Walters |
| 7,607,207 B2 | 10/2009 | Buttau et al. |
| 7,648,315 B2 | 1/2010 | Omi et al. |
| 7,658,740 B2 | 2/2010 | Shores et al. |
| 7,690,999 B2 | 4/2010 | Nozaki et al. |
| 7,743,960 B2 * | 6/2010 | Whitman et al. .......... 227/180.1 |
| 7,770,775 B2 * | 8/2010 | Shelton et al. ............. 227/178.1 |
| 7,918,230 B2 * | 4/2011 | Whitman et al. .............. 128/898 |
| 7,963,433 B2 * | 6/2011 | Whitman et al. .......... 227/178.1 |
| 7,992,758 B2 * | 8/2011 | Whitman et al. .......... 227/178.1 |
| 8,020,743 B2 * | 9/2011 | Shelton, IV ............... 227/180.1 |
| 2001/0005068 A1 | 6/2001 | Gifford et al. |
| 2001/0037114 A1 | 11/2001 | Dinger et al. |
| 2001/0039427 A1 | 11/2001 | Dinger et al. |
| 2001/0041321 A1 | 11/2001 | Segal |
| 2001/0042964 A1 | 11/2001 | Bedi et al. |
| 2001/0050465 A1 | 12/2001 | Gifford et al. |
| 2002/0003992 A1 | 1/2002 | Omi |
| 2002/0006830 A1 | 1/2002 | Buhren |
| 2002/0010433 A1 | 1/2002 | Johnson et al. |
| 2002/0032436 A1 | 3/2002 | Mogg |
| 2002/0058958 A1 | 5/2002 | Walen |
| 2002/0093151 A1 | 7/2002 | Monge |
| 2002/0109308 A1 | 8/2002 | Ochoa |
| 2002/0128610 A1 | 9/2002 | Owades |
| 2002/0151902 A1 | 10/2002 | Riedel et al. |
| 2002/0165435 A1 | 11/2002 | Weiss |
| 2002/0165549 A1 | 11/2002 | Owusu-Akyaw et al. |
| 2003/0040784 A1 | 2/2003 | Pasternak et al. |
| 2003/0047891 A1 | 3/2003 | Tomoni |
| 2003/0073502 A1 | 4/2003 | Barnley et al. |
| 2003/0077935 A1 | 4/2003 | Stein et al. |
| 2003/0077943 A1 | 4/2003 | Osypka |
| 2003/0130677 A1 | 7/2003 | Whitman et al. |
| 2003/0165794 A1 | 9/2003 | Matoba |
| 2003/0171815 A1 | 9/2003 | Kana et al. |
| 2003/0190581 A1 | 10/2003 | Segal |
| 2004/0038175 A1 | 2/2004 | Hickok |
| 2004/0049162 A1 | 3/2004 | Fisher |
| 2004/0052598 A1 | 3/2004 | Haimer |
| 2004/0057806 A1 | 3/2004 | Campbell, Jr. et al. |
| 2004/0075225 A1 | 4/2004 | Heim |
| 2004/0092991 A1 | 5/2004 | Deng |
| 2004/0162149 A1 | 8/2004 | Bayer et al. |
| 2004/0166464 A1 | 8/2004 | Schneider |

| | | | |
|---|---|---|---|
| 2004/0167478 A1 | 8/2004 | Mooney et al. | |
| 2004/0176739 A1 | 9/2004 | Stephens et al. | |
| 2004/0215058 A1 | 10/2004 | Zirps et al. | |
| 2004/0230267 A1 | 11/2004 | Wenger | |
| 2004/0260355 A1 | 12/2004 | Holleman et al. | |
| 2004/0260373 A1 | 12/2004 | Ries et al. | |
| 2004/0262856 A1 | 12/2004 | Cantlon | |
| 2004/0262857 A1 | 12/2004 | Lopez | |
| 2005/0017049 A1 | 1/2005 | Betz | |
| 2005/0021047 A1 | 1/2005 | Voss et al. | |
| 2005/0025590 A1 | 2/2005 | Spadaccini | |
| 2005/0131357 A1 | 6/2005 | Denton et al. | |
| 2005/0272280 A1 | 12/2005 | Osypka | |
| 2005/0282102 A1 | 12/2005 | Kert | |
| 2006/0015130 A1 | 1/2006 | Voorhees, Jr. et al. | |
| 2006/0020211 A1 | 1/2006 | Tokumoto et al. | |
| 2006/0024639 A1 | 2/2006 | Pond | |
| 2006/0025792 A1 | 2/2006 | Gibson et al. | |
| 2006/0025793 A1 | 2/2006 | Gibson et al. | |
| 2006/0041268 A1 | 2/2006 | Shores et al. | |
| 2006/0068361 A1 | 3/2006 | Bergler et al. | |
| 2006/0105844 A1 | 5/2006 | Sweet et al. | |
| 2006/0110706 A1 | 5/2006 | Jorneus et al. | |
| 2006/0175773 A1 | 8/2006 | Tsai et al. | |
| 2006/0223640 A1 | 10/2006 | Bassett et al. | |
| 2006/0225540 A1 | 10/2006 | Tsai et al. | |
| 2006/0287116 A1 | 12/2006 | White | |
| 2007/0023477 A1 | 2/2007 | Whitman | |
| 2007/0054232 A1 | 3/2007 | Rauchenzauner | |
| 2007/0106301 A1 | 5/2007 | Charles et al. | |
| 2007/0108706 A1 | 5/2007 | Cornwell et al. | |
| 2007/0145694 A1 | 6/2007 | Ullrich et al. | |
| 2007/0152408 A1 | 7/2007 | Peters | |
| 2007/0203477 A1 | 8/2007 | Lechot | |
| 2007/0205681 A1 | 9/2007 | Corbin, III | |
| 2007/0277988 A1 | 12/2007 | Stoetzer | |
| 2007/0290458 A1 | 12/2007 | Chuang | |
| 2008/0003537 A1 | 1/2008 | Papanek et al. | |
| 2008/0004617 A1 | 1/2008 | Hagg et al. | |
| 2008/0045972 A1 | 2/2008 | Wagner et al. | |
| 2008/0054575 A1 | 3/2008 | Hartmann | |
| 2008/0058801 A1 | 3/2008 | Taylor et al. | |
| 2008/0064007 A1 | 3/2008 | Carron et al. | |
| 2008/0070704 A1 | 3/2008 | Muller et al. | |
| 2008/0082138 A1 | 4/2008 | Smits | |
| 2008/0097409 A1 | 4/2008 | Stephens | |
| 2008/0118315 A1 | 5/2008 | Brunson | |
| 2008/0145162 A1 | 6/2008 | Mihic | |
| 2008/0146353 A1 | 6/2008 | Boffelli et al. | |
| 2008/0171603 A1 | 7/2008 | Kneeshaw et al. | |
| 2008/0179841 A1 | 7/2008 | Chen | |
| 2008/0199356 A1 | 8/2008 | Suter | |
| 2008/0208195 A1 | 8/2008 | Shores et al. | |
| 2008/0220392 A1 | 9/2008 | Carron et al. | |
| 2008/0251561 A1 | 10/2008 | Eades et al. | |
| 2008/0292418 A1 | 11/2008 | Kay et al. | |
| 2008/0314642 A1 | 12/2008 | Rodney | |
| 2009/0022562 A1 | 1/2009 | Chin | |
| 2009/0030271 A1 | 1/2009 | Foley et al. | |
| 2009/0042162 A1 | 2/2009 | Pond | |
| 2009/0054890 A1 | 2/2009 | DeCarlo | |
| 2009/0082772 A1 | 3/2009 | Ferreira | |
| 2009/0118784 A1 | 5/2009 | Alexander et al. | |
| 2009/0143785 A1 | 6/2009 | Chang et al. | |
| 2009/0145947 A1 | 6/2009 | Scirica et al. | |
| 2009/0179063 A1 | 7/2009 | Milliman et al. | |
| 2009/0194954 A1 | 8/2009 | Hsu | |
| 2009/0221873 A1 | 9/2009 | Mcgrath | |
| 2009/0224492 A1 | 9/2009 | Lin | |
| 2009/0228087 A1 | 9/2009 | Malinowski | |
| 2009/0234490 A1 | 9/2009 | Suprock et al. | |
| 2009/0248126 A1 | 10/2009 | Nippoldt et al. | |
| 2009/0261539 A1 | 10/2009 | Paulsen | |
| 2009/0273146 A1 | 11/2009 | Dezheng et al. | |
| 2009/0279973 A1 | 11/2009 | Erickson | |
| 2009/0311061 A1 | 12/2009 | Santamarina et al. | |
| 2009/0315281 A1 | 12/2009 | Tuauden et al. | |
| 2010/0015568 A1 | 1/2010 | Carron et al. | |
| 2010/0052269 A1 | 3/2010 | Zaiser et al. | |
| 2010/0056986 A1 | 3/2010 | Allen et al. | |
| 2010/0081108 A1 | 4/2010 | Webster | |
| 2010/0089974 A1 | 4/2010 | Shelton | |
| 2010/0094260 A1 | 4/2010 | Cude et al. | |

FOREIGN PATENT DOCUMENTS

| | | |
|---|---|---|
| EP | 2 098 170 A2 | 9/2009 |
| WO | WO 2007/014355 A2 | 2/2007 |
| WO | WO 2009/039506 A1 | 3/2009 |

OTHER PUBLICATIONS

The extended European Search Report corresponding to European Application No. EP 10252037.6, completed Mar. 1, 2011; mailed Mar. 9, 2011; (3 Pages).

* cited by examiner

ADAPTER FOR POWERED SURGICAL DEVICES

CROSS REFERENCE TO RELATED APPLICATION

The present application claims the benefit of and priority to U.S. Provisional Application Ser. No. 61/409,132 filed on Nov. 2, 2010, the entire contents of which are incorporated herein by reference.

BACKGROUND

1. Technical Field

The present disclosure relates to a surgical device and, more particularly, to an adapter assembly for selectively interconnecting a surgical end effector and a powered actuator device.

2. Background of Related Art

A number of proprietary drive systems for operating surgical devices that clamp tissue between opposing jaw structures and then join tissue by surgical fasteners have been developed by various surgical device manufacturers. Many of the existing surgical end effectors used in performing, for example, endo-gastrointestinal anastomosis procedures, end-to-end anastomosis procedures and transverse anastomosis procedures, typically require linear driving force in order to be operated.

Generally, the stapling operation is effected by cam bars that travel longitudinally through the staple cartridge and act upon staple pushers to sequentially eject the staples from the staple cartridge. Such cam bars are typically actuated by a trigger squeezed by an operator or a powered actuator device that provides rotary motion to deliver driving force. In the case of a powered actuator device that uses rotary motion to deliver driving force the rotary motion is not compatible with surgical end effectors that require linear driving force.

As such, in order to make the linear driven surgical end effectors compatible with the powered actuator devices that use rotary motion to deliver driving force, adapter assemblies that convert the output features of the powered actuator devices to match the work input requirements of end effectors are required.

SUMMARY

In accordance with an embodiment of the present disclosure, there is provided an adapter assembly for selectively interconnecting a surgical end effector and a powered actuator device. The adapter assembly includes a first drive converter assembly configured to convert a rotation of a first drive shaft of the powered actuator device into an axial translation of a first drive member of the surgical end effector and a second drive converter assembly configured to convert a rotation of a second drive shaft of the powered actuator device into an axial translation of a second drive member of the surgical end effector. The first drive converter assembly is at least partially disposed within the second drive converter assembly, wherein the first drive converter assembly and the second drive converter assembly are configured to rotate and translate independent of each other.

The adapter assembly may further include first and second drive rods configured to be coupled with the rotatable first and second drive shafts of the powered actuator device, respectively. The first drive rod engages the first drive converter assembly and the second drive rod engages the second drive converter assembly.

The first and second drive rods may each include a pinion gear portion. The first drive converter assembly may include an actuation shaft defining a worm gear portion. The first drive rod supports a pinion gear portion, wherein the worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

Similarly, the second drive converter assembly may include an elongate tube defining a worm gear portion. The second drive rod supports a pinion gear portion, wherein the worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

The first and second drive rods may be flexible and capable of transmitting rotational forces. In addition, a distal end of the adapter assembly may be configured for a selective, detachable fitting with the surgical end effector.

In accordance with another aspect of the present disclosure, there is provided a surgical device including a powered actuator device including at least two rotatable drive shafts, a surgical end effector including at least two axially translatable drive members and an adapter assembly including a first drive converter assembly and a second drive converter assembly. The first drive converter assembly is configured to convert rotation of a first drive shaft of the powered actuator device into an axial translation of a first drive member of the surgical end effector. The second drive converter assembly is configured to convert rotation of a second drive shaft of the powered actuator device into an axial translation of a second drive member of the surgical end effector, wherein the first drive converter assembly is at least partially disposed within the second drive converter assembly.

The adapter assembly may further include first and second drive rods configured to be operatively coupled with the rotatable first and second drive shafts of the powered actuator device, respectively. The first drive rod engages the first drive converter assembly and the second drive rod engages second drive converter assembly.

The first and second drive rods may each include a pinion gear portion. Moreover, the first drive converter assembly may include an actuation shaft defining a worm gear portion, wherein the first drive rod supports a pinion gear portion. The worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

Similarly, the second drive converter assembly may include an elongate tube defining a worm gear portion, wherein the second drive rod supports a pinion gear portion. The worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

The first and second drive rods may be flexible and capable of transmitting rotational forces. In addition, a distal end of the adapter assembly may be configured for a selective, detachable fitting with the surgical end effector.

BRIEF DESCRIPTION OF THE DRAWINGS

The foregoing objects, features and advantages of the disclosure will become more apparent from a reading of the following description in connection with the accompanying drawings, in which.

DETAILED DESCRIPTION OF EMBODIMENTS

Figure 1:
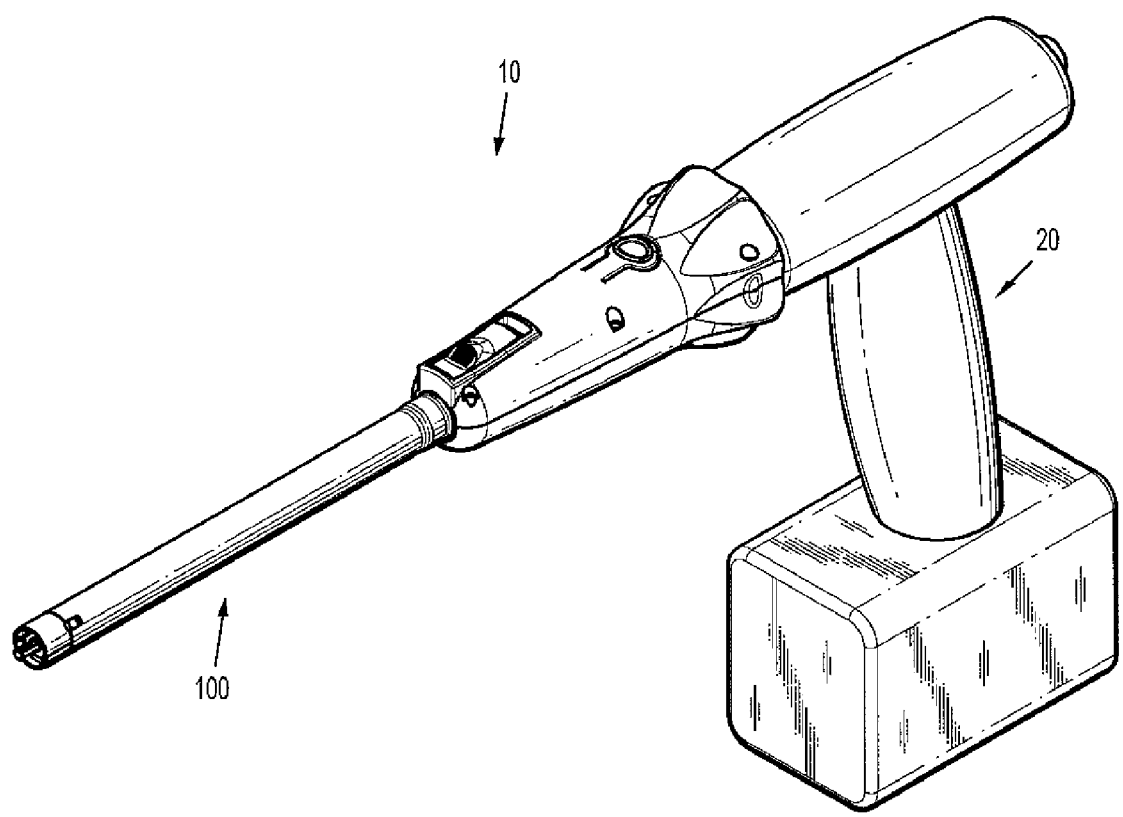
FIG. 1 is a perspective view of a surgical device including an adapter assembly according to an embodiment of the present disclosure.

Embodiments of the presently disclosed adapter assemblies for surgical devices are described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Referring now to FIG. 1, there is disclosed a powered surgical instrument generally referred to as 10. In the interest of brevity, this disclosure will focus primarily on a mechanical adapter assembly 100 for selectively interconnecting a surgical end effector and a powered actuator device 20. For a detailed description of the construction and operation of exemplary powered surgical instrument 10 for use with adapter assembly 100, reference may be made to U.S. Patent Application Publication No. 2007/0023477, the entire content of which is incorporated herein by reference.

Figure 2:
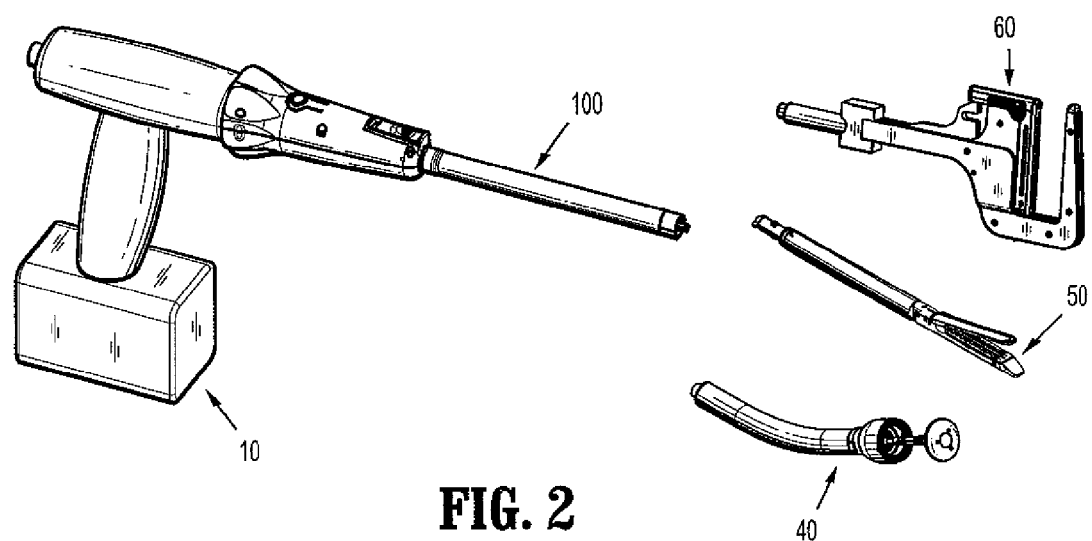
FIG. 2 is a perspective view of the surgical device of FIG. 1, illustrating the potential use with various surgical end effectors.
Figure 3:
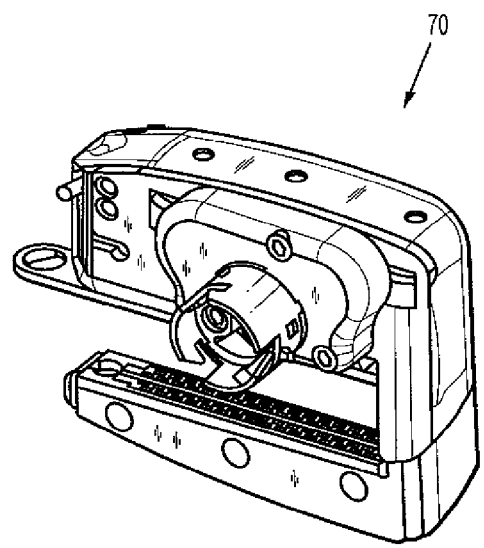
FIG. 3 is a perspective view of a right angled linear cutter/stapler end effector for use with an adapter assembly according to an embodiment of the present disclosure.

With reference to FIGS. 1-3, powered surgical instrument 10 generally includes a powered actuator device 20 and mechanical adapter assembly 100 selectively interconnecting any one of surgical end effectors 40, 50, 60, 70 and powered actuator device 20. Any one of end effectors 40, 50, 60, 70 may be releasably secured to a distal end of adapter assembly 100. Each end effector 40, 50, 60, 70 includes a cartridge assembly housing a plurality of surgical fasteners or staples and an anvil assembly movably secured in relation to the cartridge assembly. Powered actuator device 20 includes a housing, at least one drive motor, at least one energy source for powering the at least one drive motor, and at least one rotatable drive shaft connected to the at least one drive motor. In use, the actuation of the drive motor results in an actuation of an end effector 40, 50, 60, 70 attached thereto, to apply staples to tissue and to optionally cut tissue.

Figure 4:
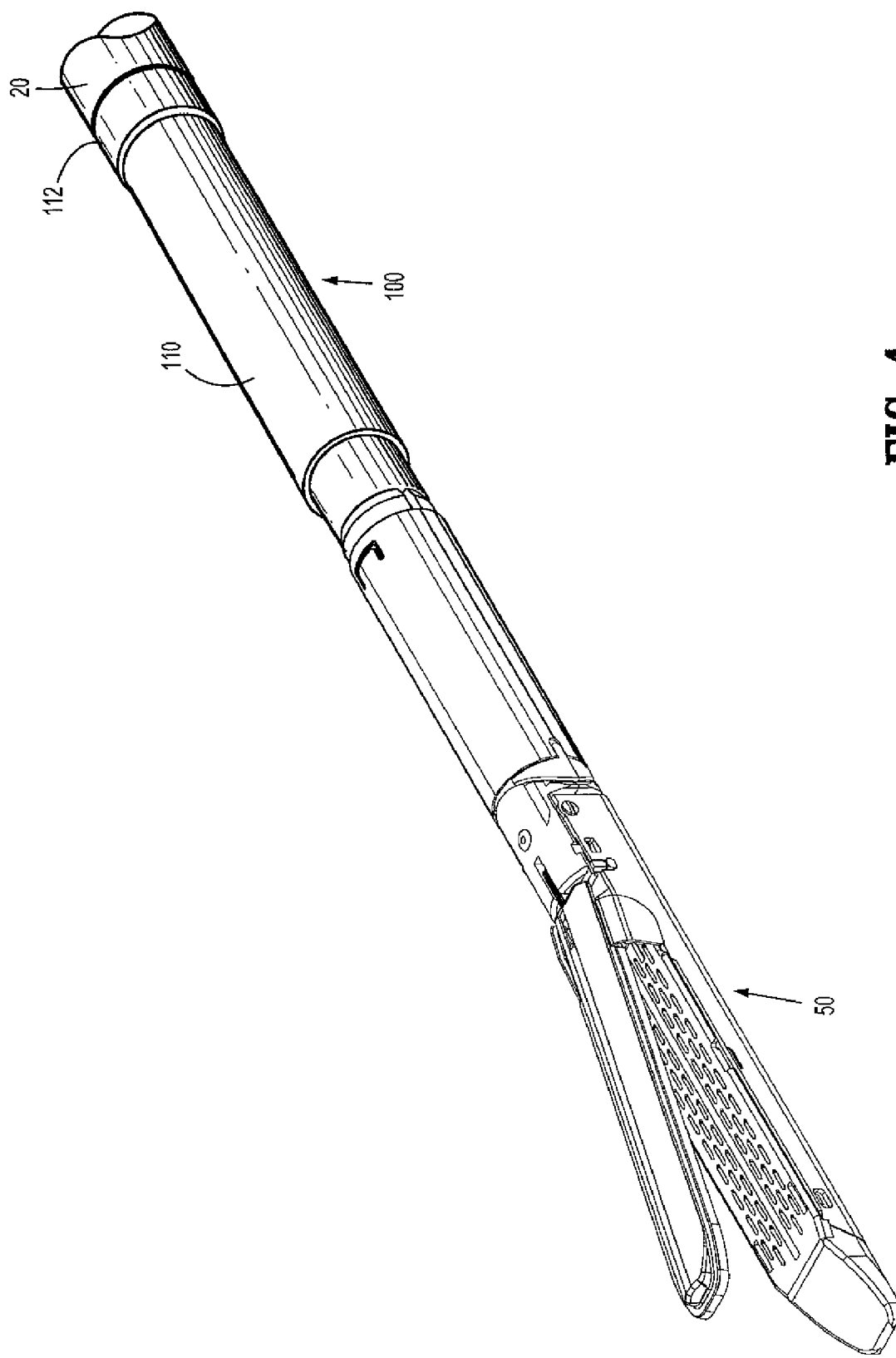
FIG. 4 is a perspective view of an adapter assembly according to an embodiment of the present disclosure having a surgical end effector connected thereto.
Figure 5:
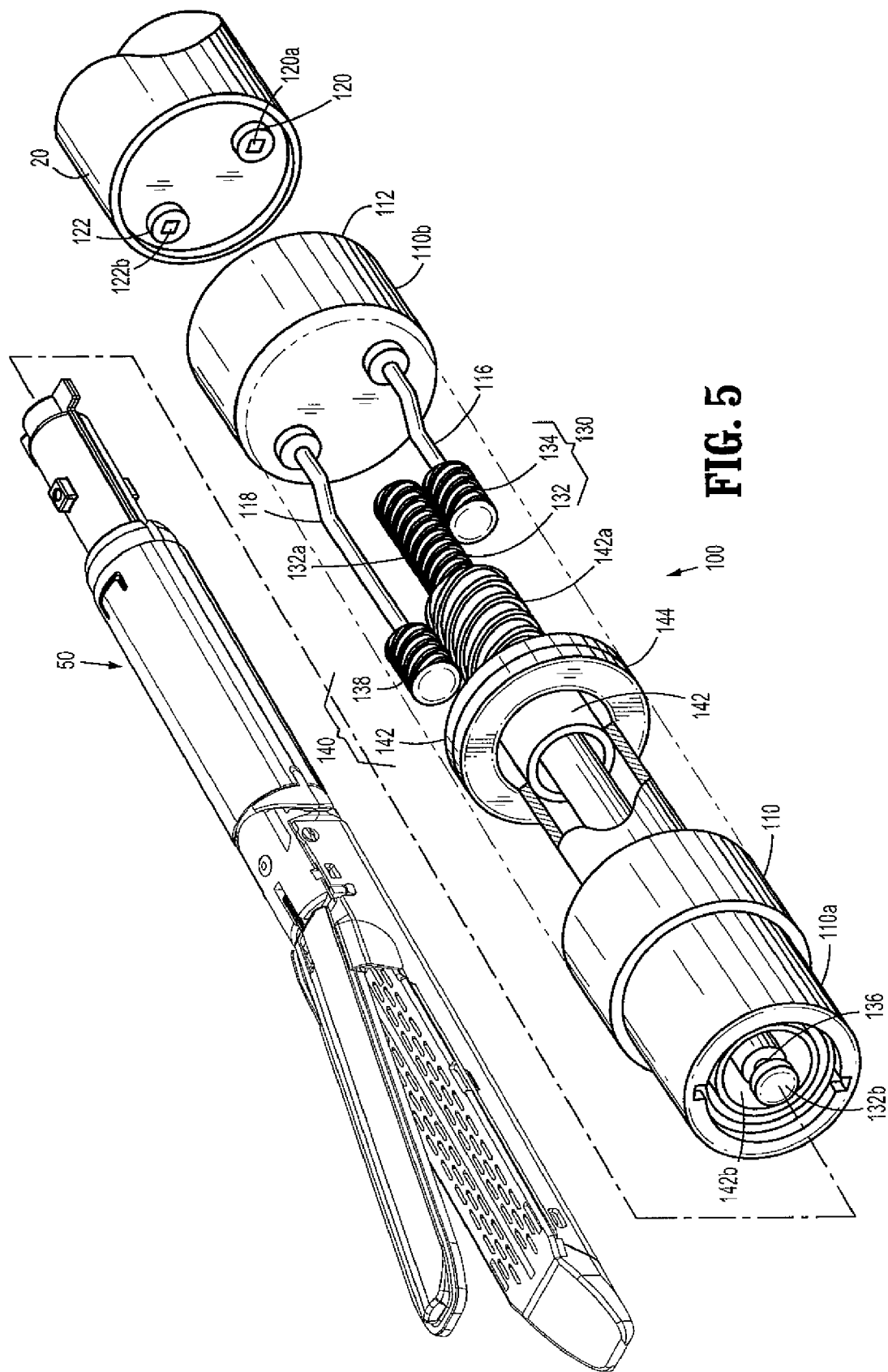
FIG. 5 is an enlarged perspective view of the adapter assembly of FIG. 4 shown with an outer tube removed therefrom.
Figure 6:
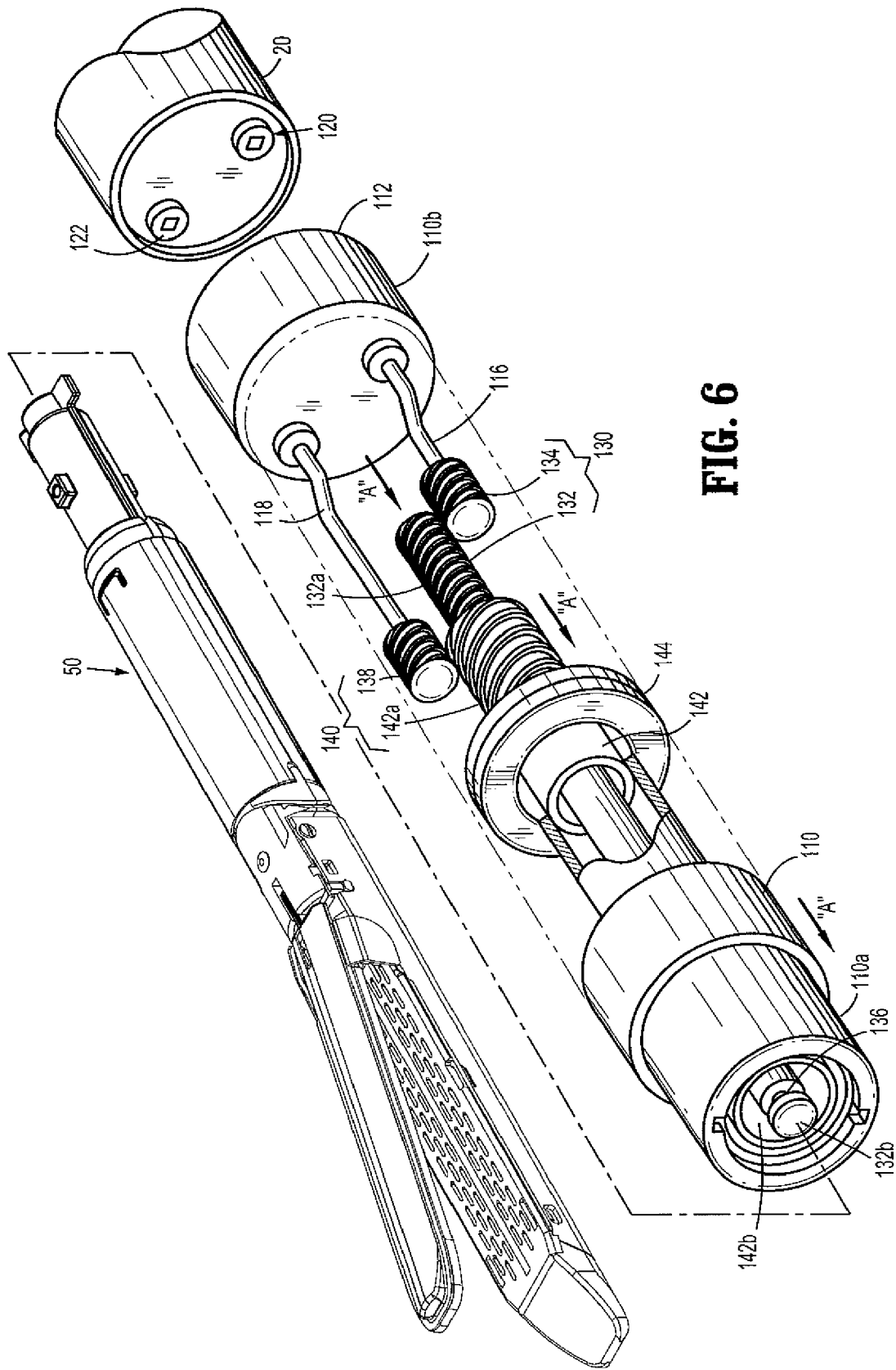
FIG. 6 is an enlarged perspective view of the adapter assembly of FIG. 5 illustrating an independent axial translation of an actuation shaft and an inner tube thereof.

With reference to FIGS. 4, 5 and 6, an adapter assembly in accordance with an embodiment of the present disclosure is shown generally as 100. As shown in FIGS. 4-6, adapter assembly 100 is operatively connected to a distal end of powered actuator device 20, and surgical end effector 50 is selectively coupled to a distal end of adapter assembly 100. However, adapter assembly 100 is configured to operatively interconnect any one of a number of surgical end effectors to powered actuator device 20, as seen in FIG. 2. For example, adapter assembly 100 may operatively interconnect and couple powered actuator device 20 to an endo-gastrointestinal anastomosis end effector 40 or a transverse anastomosis end effector 60, both of which require linear driving force.

Each of end effectors 40, 50, 60 includes an axially translatable drive member to fire end effectors 40, 50, 60 to expel staples contained in the cartridge assembly for formation against the anvil assembly and/or to actuate a knife blade along the staple line. End effectors 40, 50, 60 may include an additional axially translatable drive member that is configured to open and close the jaw assemblies by approximating at least one of the anvil assembly and the cartridge assembly to and away from one another. The additional axially translatable drive member may also be configured to cause articulation of end effectors 40, 50, 60.

Adapter assembly 100 may be configured to operatively interconnect with a surgical end effector requiring a linear driving force, but may also be adaptable to be operatively coupled to an end effector requiring a rotational driving force for an operation thereof, such as, for example, a right angled linear cutter/stapler end effector 70, as shown in FIG. 3. Right angled linear cutter/stapler end effector 70 includes a rotatable drive member for firing end effector 70 to expel staples contained in the cartridge assembly for formation against the anvil assembly. End effector 70 may include additional rotatable drive members to actuate a knife blade along the staple line and/or to open and close the jaw assemblies by approximating at least one of the anvil assembly and the cartridge assembly to and away from one another.

With reference still to FIGS. 4-6, a detailed description of the construction and operation of adapter assembly 100 is provided. Adapter assembly 100 includes a tube housing 110 configured to house the components of adapter assembly 100 and dimensioned such that tube housing 110 may pass through a typical trocar port, cannula or the like. Tube housing 110 includes a distal end portion 110a that is operatively coupled to end effector 50 and a proximal end portion 110b that is coupled to powered actuator device 20.

In particular, as seen in FIGS. 5 and 6, adapter assembly 100 further includes a drive coupling assembly 112 at a proximal end portion thereof, which operatively couples adapter assembly 100 to powered actuator device 20. Drive coupling assembly 112 includes rotatably supported and distally extending first and second proximal drive shafts 116, 118, respectively. Proximal drive shafts 116, 118 may be made flexible to act as shock absorbers allowing for reduced peak loads, yet sufficiently rigid to transmit rotational forces. First and second proximal drive shafts 116, 118 each include at a proximal portion thereof a tapered neck portion (not shown) having a non-circular cross-sectional profile, e.g., square shaped. Each of first and second proximal drive shafts 116, 118 is provided with a biasing means (not shown) disposed about the respective neck portion and a sleeve (not shown) disposed proximal of the biasing means. The sleeves each define a bore having a cross-sectional profile that corresponds to that of the neck portion of proximal drive shafts 116, 118. The distal ends of the first and second drive shafts of powered actuator device 20 include coupling cuffs 120, 122, each defining a recess 120a, 122a corresponding to the non-circular cross-sectional profile of the neck portion of proximal drive shafts 116, 118. Coupling cuffs 120, 122 of actuator device 20 engage the proximal end portions (not shown) of proximal drive shafts 116, 118 (wherein each proximal end portion of the proximal drive shafts 116, 118 has a non-circular cross-sectional profile for engaging respective recess 120a, 122a of coupling cuffs 120, 122), whereby rotation of drive shafts (not shown) of powered actuator device 20 results in concomitant rotation of coupling cuffs 120, 122 and concomitant rotation of first and second proximal drive shafts 116, 118.

With continued reference to FIGS. 5 and 6, adapter assembly 100 further includes first and second drive converter assemblies 130, 140. Each drive converter assembly 130, 140 is configured to convert rotation of respective first and second drive shafts of powered actuator device 20 and concomitant rotation of respective first and second proximal drive shafts 116, 118 into axial translation of respective drive members of end effector 50.

The first drive converter assembly 130 includes an actuation shaft 132 translatably supported for axial reciprocation within an inner tube 142 of drive converter assembly 140 by any number of appropriately positioned and sized bearings and/or bushings (not shown). The coaxial relationship of actuation shaft 132 and inner tube 142 allows for axially rotational displacement thereof without adverse end effector 50 actuation or spatial conflict therebetween. Actuation shaft 132 includes a worm-gear portion 132a at a proximal end region of actuation shaft 132 and a distal end portion 132b defining a connection member 136 configured for selective engagement with an axially translatable drive member of end effector 50. First drive converter assembly 130 further includes a pinion or worm gear portion 134 provided at a distal end portion of first proximal drive shaft 116. Pinion gear portion 134 engages worm gear portion 132a at a proximal end region of actuation shaft 132.

In operation, as seen in FIGS. 5 and 6, the activation/rotation of a first drive shaft (not shown) of powered surgical device 20 results in concomitant rotation of first proximal drive shaft 116 of adapter assembly 100. As first proximal drive shaft 116 is rotated, first proximal drive shaft 116 causes rotation of pinion gear portion 134. Since pinion gear portion 134, at a distal end portion of first proximal drive shaft 116, engages worm gear portion 132a of actuation shaft 132, rotation of pinion gear portion 134 causes axial translation of actuation shaft 132. It is contemplated that the actuation shaft 132 is supported by any number of appropriately positioned and sized bearings and bushings (not shown) that enable axial translation in the direction of "A" as shown in FIG. 6. Accordingly, with connection member 136 of actuation shaft 132 connected to a first drive member of end effector 50, axial translation of actuation shaft 132 causes concomitant axial translation of the first drive member of end effector 50 to effectuate an operation and/or function thereof, such as, for example, firing of the end effector 50.

Upon completion of the operation and/or function of the first drive member of end effector 50, e.g., firing of end effector 50, actuation shaft 132 may be retracted to its initial position for subsequent operation thereof. The first drive shaft (not shown) of powered surgical device 20 is reactivated causing rotation thereof in the direction opposite to that when actuation shaft 132 was axially translated in the distal direction. The concomitant rotation of first proximal drive shaft 116 of adapter assembly 100 causes rotation of pinion gear portion 134. Pinion gear portion 134 engages worm gear portion 132a of actuation shaft 132 and causes axial translation of actuation shaft 132 in a proximal direction until actuation shaft 132 reaches the initial position.

With continued reference to FIGS. 5 and 6, second drive converter assembly 140 includes an inner tube 142 rotatably supported by rotary plates 144 or by any number of appropriately positioned and sized bearings or bushings (not shown) for axial reciprocation of inner tube 142 within tube housing 110. Inner tube 142 includes a worm-gear portion 142a at a proximal end region of inner tube 142 and a distal end portion 142b disposed at a distal end of tube housing 110. Second drive converter assembly 140 further includes a pinion or worm gear 138 provided at a distal end portion of second proximal drive shaft 118. Worm-gear portion 142a of inner tube 142 engages pinion gear 138 for axial reciprocation of inner tube 142 within tube housing 110.

In operation, as seen in FIGS. 5 and 6, the activation/rotation of a second drive shaft (not shown) of powered surgical device 20 results in concomitant rotation of second proximal drive shaft 118 of adapter assembly 100. As second proximal drive shaft 118 is rotated due to rotation of the second drive shaft of powered actuator device 20, pinion gear 138 of second drive converter assembly 150 is caused to be rotated. Since pinion gear 138, at a distal end portion of second proximal drive shaft 118, engages worm gear portion 142a of inner tube 142, rotation of pinion gear portion 138 causes axial translation of inner tube 142 independently of actuation shaft 132, in the direction of arrow "A" as shown in FIG. 6. Accordingly, as inner tube 142 is translated axially, with the distal end of inner tube 142 connected to a second drive member of end effector 50, inner tube 142 causes concomitant axial translation of the second drive member of end effector 50 to effectuate an additional operation thereof, such as, for example, articulation of the end effector and/or approximation of the pair of jaws, independent of the operation effected by actuation shaft 132.

Upon completion of the operation and/or function of the second drive member of end effector 50, e.g., articulation of end effector 50 and/or approximation of the pair of jaws, inner tube 142 may be retracted to its initial position for subsequent operation thereof. The second drive shaft (not shown) of powered surgical device 20 is reactivated causing rotation thereof in the direction opposite to that when inner tube 142 was axially translated in the distal direction. The concomitant rotation of second proximal drive shaft 118 of adapter assembly 100 causes rotation of pinion gear portion 138. Pinion gear portion 138 engages worm gear portion 142a of inner tube 142 and causes axial translation of inner tube 142 in a proximal direction until inner tube 142 reaches the initial position.

Actuation shaft 132 is dimensioned to be concentrically arranged within inner tube 142 which allows for a compact design of adapter assembly 100 and independent coaxial translation of actuation shaft 132 with respect to inner tube 142. Actuation shaft 132 may further include a pair of flanges (not shown) extending radially, so that the pair of flanges restrict the range of axial translation of actuation shaft 132 in conjunction with an inwardly extending flange (not shown) formed within inner tube 142, whereby a proximal end of actuation shaft 132 is prevented from being driven into drive coupling assembly 112 and/or from distally disengaging pinion gear 134 of first proximal drive shaft 116. Moreover, the placement of the flanges may be tailored to meet the needs of a particular end effector to take into account, e.g., the required travel distance of the particular axially translatable drive member of the surgical end effector.

Similarly, inner tube 142 may further include radially extending flanges (not shown) such that inner tube 142 reciprocates axially inside tube housing 110 within a predetermined ranged. Under such design, inner tube 142 is prevented from being driven distally into pinion gear 134 on first proximal drive shaft 116 and from distally disengaging pinion gear 138 on second proximal drive shaft 122. Moreover, such design allows inner tube 142 to translate only the distance required to effectuate an operation of the drive member of end effector 50.

In accordance with the present disclosure, it is contemplated that the adapter assembly 100 may incorporate a transmission or gearing portion to optimize the rotational speed and torque or the linear speed and force to control and manipulate specific end effectors. Furthermore, the pitch and helix angle of the worm gear can be configured to provide additional speed and/or force refinements as needed.

It is further contemplated that the proximal and distal ends of adapter assembly 100 may be operatively coupled to powered actuator device 20 and any one of end effectors 40, 50, 60, 70, respectively, using a variety of attachment features, such as, for example, a bayonet coupling, latch, detent or snap-fit. In addition, adapter assembly 100 may include a lock mechanism (not shown) configured to fix the axial position and radial orientation of actuation shaft 132 for the connection and disconnection of end effectors 40, 50, 60, 70 thereto. Still further, axial rotation of the entire tube housing 110 can be accomplished by engaging rotary power from the power actuator (if available) or by manually turning the tube housing.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. An adapter assembly for selectively interconnecting a surgical end effector and a powered actuator device, the adapter assembly comprising:
 a first drive converter assembly configured to convert a rotation of a first drive shaft of the powered actuator device into an axial translation of a first drive member of the surgical end effector; and
 a second drive converter assembly configured to convert a rotation of a second drive shaft of the powered actuator device into an axial translation of a second drive member of the surgical end effector, the first drive converter assembly being at least partially disposed within the second drive converter assembly, wherein the first drive converter assembly and the second drive converter assembly are configured to rotate and translate independent of each other.

2. The adapter assembly of claim 1, further comprising first and second drive rods configured to be coupled with the rotatable first and second drive shafts of the powered actuator device, respectively, wherein the first drive rod engages the first drive converter assembly and the second drive rod engages the second drive converter assembly.

3. The adapter assembly of claim 2, wherein the first and second drive rods each include a pinion gear portion.

4. The adapter assembly of claim 3, wherein the first drive converter assembly includes an actuation shaft defining a worm gear portion, and wherein the first drive rod supports a pinion gear portion, wherein the worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

5. The adapter assembly of claim 3, wherein the second drive converter assembly includes an elongate tube defining a worm gear portion, and wherein the second drive rod supports a pinion gear portion, wherein the worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

6. The adapter assembly of claim 2, wherein the first and second drive rods are flexible and capable of transmitting rotational forces.

7. The adapter assembly of claim 1, wherein a distal end of the adapter assembly is configured for a selective, detachable fitting with the surgical end effector.

8. A surgical device, comprising:
 a powered actuator device including at least two rotatable drive shafts;
 a surgical end effector including at least two axially translatable drive members; and
 an adapter assembly including a first drive converter assembly and a second drive converter assembly, the first drive converter assembly being configured to convert rotation of a first drive shaft of the powered actuator device into an axial translation of a first drive member of the surgical end effector, the second drive converter assembly being configured to convert rotation of a second drive shaft of the powered actuator device into an axial translation of a second drive member of the surgical end effector, wherein the first drive converter assembly is at least partially disposed within the second drive converter assembly.

9. The surgical device of claim 8, wherein the adapter assembly further includes first and second drive rods configured to be operatively coupled with the rotatable first and second drive shafts of the powered actuator device, respectively, wherein the first drive rod engages the first drive converter assembly and the second drive rod engages second drive converter assembly.

10. The surgical device of claim 9, wherein the first and second drive rods each include a pinion gear portion.

11. The surgical device of claim 10, wherein the first drive converter assembly includes an actuation shaft defining a worm gear portion, and wherein the first drive rod supports a pinion gear portion, wherein the worm gear portion of the actuation shaft engages the pinion gear portion of the first drive rod, whereby rotation of the first drive shaft of the powered actuator device rotates the pinion gear portion of the first drive rod to effectuate axial translation of the actuation shaft which in turn axially translates the first drive member of the surgical end effector.

12. The surgical device of claim 10, wherein the second drive converter assembly includes an elongate tube defining a worm gear portion, and wherein the second drive rod supports a pinion gear portion, wherein the worm gear portion of the elongate tube engages the pinion gear portion of the second drive rod, whereby rotation of the second drive shaft of the powered actuator device rotates the pinion gear portion of the second drive rod to effectuate axial translation of the elongate tube which in turn axially translates the second drive member of the surgical end effector.

13. The surgical device of claim 9, wherein the first and second drive rods are flexible and capable of transmitting rotational forces.

14. The surgical device of claim 8, wherein a distal end of the adapter assembly is configured for a selective, detachable fitting with the surgical end effector.

* * * * *